(12) United States Patent
Fossa

(10) Patent No.: US 6,384,039 B1
(45) Date of Patent: May 7, 2002

(54) QT DISPERSION AND HEART RATE VARIABILITY IMPROVEMENT WITH CRF ANTAGONISTS TO PREVENT SUDDEN DEATH

(75) Inventor: Anthony A. Fossa, Mystic, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/540,439

(22) Filed: Mar. 31, 2000

Related U.S. Application Data

(60) Provisional application No. 60/127,659, filed on Aug. 2, 1999.

(51) Int. Cl.[7] ...................... A61K 31/505; A61K 31/52; A61K 31/41
(52) U.S. Cl. ....................... 514/256; 514/256; 514/261; 514/384
(58) Field of Search ............................... 514/256, 261, 514/384

(56) References Cited

U.S. PATENT DOCUMENTS 5,063,245 A 11/1991 Abreu et al. ................. 514/404

FOREIGN PATENT DOCUMENTS

| EP | 0773023 | 5/1997 | ......... A61K/31/435 |
| WO | WO 9413676 | 6/1994 | ......... C07D/487/04 |
| WO | WO 9413677 | 6/1994 | ......... C07D/487/04 |
| WO | 9533750 | 12/1995 | ......... C07D/487/04 |
| WO | 9534563 | 12/1995 | ......... C07D/471/04 |
| WO | WO-9744038 A1 * | 11/1997 | |

OTHER PUBLICATIONS

Mallet E. "Hypocalcemia in infants and children" Revue Du Praticien, Apr.13, 1989, 39 (11) 942–8, ISSN: 0035–2640.*

Strijbos et al. "Corticotrophin–releasing factor antagonist inhibits neuronal damage induced by focal cerebral ischemia or activation of NMDA receptors in the rat brain" Brain Res. (1994), 656 (2), 405–8. SSN: 0006–8993.*

Maron et al. "Blunt impact to the chest leading to sudden death from cardiac arrest during sports activities." New England Journal of Medicine, (1995) 333/6 (337–342). ISSN: 0028–4793.*

* cited by examiner

Primary Examiner—Theodore J. Criares
Assistant Examiner—Jennifer Kim
(74) Attorney, Agent, or Firm—Peter C. Richardson; Gregg C. Benson; Gregory P. Raymer

(57) ABSTRACT

A method of preventing sudden death which comprises administering to a mammal, including a human, a therapeutically effective amount of a corticotropin releasing factor antagonist.

16 Claims, No Drawings

QT DISPERSION AND HEART RATE VARIABILITY IMPROVEMENT WITH CRF ANTAGONISTS TO PREVENT SUDDEN DEATH

This application claims benefit of provisional application No. 60/127,659 filed Aug. 2, 1999.

BACKGROUND OF THE INVENTION

This invention relates to methods for reducing the incidence of sudden death in certain patients by administering thereto a pharmaceutically effective amount of a corticotropin releasing factor (CRF) antagonist. It is currently believed that CRF antagonists reduce the incidence of sudden death in patients by improving their QT dispersion and heart rate variability.

Sudden unexpected death occurs in about 50% of patients suffering from mild heart failure and in 25% of patients experiencing severe heart failure (Barr et al., *Lancet*, 343 (8893):327–29 (1994)). Regional variation in ventricular repolarization, which represents an electrophysiological substrate for arrhythmias, can be detected by inter-lead variability of the QT interval (dispersion). Increased QT interval dispersion has been shown in patients who develop ventricular tachyarrhythmias after an acute myocardial infarction, long QT syndrome, chronic heart failure, and hypertrophic cardiomyopathy (see, e.g., Potratz et al., *Eur. Heart J.*, 14:254 (1993); Day et al., *Br. Heart J.*, 63:342–44 (1990); and Buja et al., *Am. J. Cardiol.*, 72:973–976 (1993)).

The compounds of formulas I and II as described herein, their pharmaceutically acceptable salts, and methods of preparing such compounds and salts are disclosed in European patent application number EP 0773023 A1, and in more detail in PCT international patent application numbers PCT/IB95/00373 (published as WO 95/34563), PCT/IB95/00439 (published as WO 95/33750), PCT/US93/11333 (published as WO 94/13677), and PCT/US93/10715 (published as WO 94/13676). These European and PCT international patent applications, referred to above, are incorporated herein by reference in their entirety.

The foregoing PCT international patent applications refer to the use of the compounds of formulas I and II in the treatment of illnesses induced or facilitated by CRF and in the treatment of anxiety, depression, fatigue syndrome, gastrointestinal diseases, headache, pain, cancer, immune dysfunction, hemorrhagic stress, drug addiction, drug and alcohol withdrawal symptoms, fertility problems, stress-induced psychotic episodes, neurodegenerative diseases such as Alzheimer's disease, irritable bowel syndrome including Crohn's disease, spastic colon, and irritable colon, eating disorders such as anorexia nervosa, inflammatory disorders such as arthritis, asthma, and allergies.

Other CRF antagonists that can be used to treat the disorders recited in the method of this invention are referred to in PCT international patent application numbers PCT/IB95/00318 (published as WO 95/33727), PCT/IB97/00918 (published as WO 98/05661), PCT/IB97/00904 (published as WO 98/08846), and PCT/IB97/00922 (published as WO 98/08847), PCT/EP98/02267 (published as WO 98/47874), PCT/EP98/02268 (published as WO 98/47903), PCT/US98/09861 (published as WO 98/51312), PCT/US98/13840 (published as WO 99/01439), PCT/US98/13913 (published as WO 99/01454), as well as in U.S. Pat. Nos. 5,063,245, 5,109,111, 5,132,111, 5,245,009, 5,464,847, 5,493,006, 5,510,458, 5,605,642, 5,644,057, 5,663,292, 5,668,145, 5,705,646, and 5,712,303. All of the above-cited PCT international patent applications and United States Patents are incorporated herein by reference in their entirety.

The importance of CRF antagonists is set out in the literature, e.g., as discussed in U.S. Pat. No. 5,063,245, which is incorporated herein by reference in its entirety. A recent outline of the different activities possessed by CRF antagonists is found in M. J. Owens et al., *Pharm. Rev.*, 43:425–73 (1991), also incorporated herein by reference in its entirety.

PCT international patent application PCT/US98/07831 (published as WO 98/47899) discloses the usefulness of substituted pyrrolopyridines in the treatment of inflammatory diseases. The disclosed compounds inhibit the production of certain inflammatory cytokines, namely TNF-α and IL-1β. One of the listed cytokine-related inflammatory diseases is congestive heart failure. However, no mention is made of QT dispersion or heart rate variability.

SUMMARY OF THE INVENTION

The present invention relates to a method of preventing sudden death in an animal comprising administering to said animal, preferably a human, a therapeutically effective amount of a corticotropin releasing factor antagonist.

The method of the present invention is most useful in preventing sudden death in specific patients, particularly those suffering from cardiovascular or heart related diseases such as hypertension, tachycardia, congestive heart failure, and the like, as well as other diseases such as stroke, osteoporosis, premature birth, psychosocial dwarfism, stress-induced fever, ulcer, diarrhea, post-operative ileus, colonic hypersensitivity associated with psychopathological disturbance and stress, and the like. The method of the present invention is also useful in preventing sudden death in diabetic patients, as well as in patients suffering from many neurological disorders such as brain damage, Guillain-Barre syndrome, sudden infant death syndrome, congenital hypoventilation syndrome, uremic neuropathy, and the like.

In a preferred embodiment, the present invention is practiced using a compound of Formula I or II:

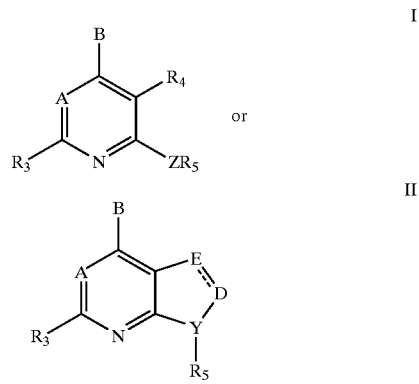

or a pharmaceutically acceptable salt thereof, wherein
the dashed line represents an optional double bond;
A is —CR$_7$ or N;
B is —NR$_1$R$_2$, —CR$_1$R$_2$R$_{11}$, —C(=CR$_1$R$_{12}$)R$_2$, —NHCR$_{11}$R$_1$R$_2$, —OCR$_{11}$R$_1$R$_2$, —SCR$_{11}$R$_1$R$_2$, —CR$_{11}$R$_2$OR$_1$, —CR$_{11}$R$_2$SR$_1$, —C(S)R$_2$, —NHNR$_1$R$_2$, —CR$_2$R$_{11}$NHR$_1$ or —C(O)R$_2$;
D is
 N or —CR$_{10}$ when a double bond connects E and D and E is —CR$_4$;

—$CR_{10}$ when a double bond connects E and D and E is N; or

—$CR_8R_9$, —$CHR_{10}$, —C=O, —C=S, —C=NH, or —C=NCH$_3$ when a single bond connects E and D;

E is —$CR_4$ or N when a double bond connects E and D, and E is —$CR_4R_6$ or —$NR_6$ when a single bond connects E and D;

Y is N or —CH;

Z is NH, O, S, —N($C_1$–$C_2$ alkyl), or —$CR_{12}R_{13}$, wherein $R_{12}$ and $R_{13}$ are each, independently, hydrogen, trifluoromethyl, or methyl, or one of $R_{12}$ and $R_{13}$ is cyano and the other is hydrogen or methyl;

$R_1$ is hydrogen or $C_1$–$C_6$ alkyl which is optionally substituted with up to two substituents independently selected from hydroxy, cyano, nitro, fluoro, chloro, bromo, iodo, $CF_3$, $C_1$–$C_4$ alkoxy, —O—CO—($C_1$–$C_4$ alkyl), —O—CO—NH($C_1$–$C_4$ alkyl), —O—CO—N($C_1$–$C_4$ alkyl)($C_1$–$C_2$ alkyl), —NH($C_1$–$C_4$ alkyl), —N($C_1$–$C_2$ alkyl)($C_1$–$C_4$ alkyl), —S($C_1$–$C_4$ alkyl), —N($C_1$–$C_4$alkyl)CO($C_1$–$C_4$ alkyl), —NHCO($C_1$–$C_4$ alkyl), —$CO_2$($C_1$–$C_4$ alkyl), —CONH($C_1$–$C_4$ alkyl), —CON($C_1$–$C_4$ alkyl)($C_1$–$C_2$ alkyl), ($C_1$–$C_4$ alkyl)sulfinyl, ($C_1$–$C_4$ alkyl)sulfonyl, and ($C_1$–$C_4$ alkyl)sulfanyl, and wherein said $C_1$–$C_6$ alkyl, $C_1$–$C_4$ alkoxy, and $C_1$–$C_4$ alkyl moieties in the foregoing $R_1$ groups optionally contain one double or triple bond;

$R_2$ is $C_1$–$C_6$ alkyl, heteroaryl, aryl, heteroaryl ($C_1$–$C_4$ alkyl), or aryl ($C_1$–$C_4$ alkyl), wherein said aryl and the aryl moiety of said (aryl)$C_1$–$C_4$ alkyl are selected from the group consisting of phenyl and naphthyl, and said heteroaryl and the heteroaryl moiety of said (heteroaryl)$C_1$–$C_4$ alkyl is selected from the group consisting of thienyl, benzothienyl, pyridyl, thiazolyl, quinolyl, pyrazinyl, pyrimidyl, imidazolyl, furanyl, benzofuranyl, benzothiazolyl, isothiazolyl, benzisothiazolyl, benzisoxazolyl, benzimidazolyl, indolyl, and benzoxazolyl; or $R^2$ is $C_3$–$C_8$ cycloalkyl or ($C_3$–$C_8$ cycloalkyl)$C_1$–$C_6$ alkyl, wherein one or two of the ring carbons of said cycloalkyl having at least 4 ring members and the cycloalkyl moiety of said ($C_3$–$C_8$ cycloalkyl)$C_1$–$C_6$ alkyl having at least 4 ring members is optionally replaced by an oxygen or sulfur atom or by –$NR_{14}$ wherein $R_{14}$ is hydrogen or $C_1$–$C_4$ alkyl; and wherein each of the foregoing $R_2$ groups is optionally substituted by up to three substituents independently selected from chloro, fluoro, and $C_1$–$C_4$ alkyl, or by one substituent selected from bromo, iodo, cyano, nitro, $C_1$–$C_6$ alkoxy, —O—CO—($C_1$–$C_4$ alkyl), —O—CO—N($C_1$–$C_4$ alkyl)($C_1$–$C_2$ alkyl), —$CO_2$ ($C_1$–$C_4$ alkyl), ($C_1$–$C_4$ alkyl)sulfanyl, ($C_1$–$C_4$ alkyl)sulfinyl, and ($C_1$–$C_4$ alkyl)sulfonyl, and wherein said $C_1$–$C_4$ alkyl and $C_1$–$C_6$ alkyl moieties of the foregoing $R_2$ groups optionally contain one carbon-carbon double or triple bond;

or $R^1$ and $R^2$ of said —$NR_1R_2$ and said —$CR_1R_2R_{11}$ are taken together to form a saturated or partially saturated 5- to 8-membered ring, wherein said ring optionally contains one or two carbon-carbon double bonds, and wherein one or two of the ring carbons is optionally replaced by a heteroatom selected from O, S, and N;

$R_3$ is hydrogen, $C_1$–$C_6$ alkyl, fluoro, chloro, bromo, iodo, hydroxy, amino, SH, —NH($C_1$–$C_4$ alkyl), —N($C_1$–$C_4$ alkyl)($C_1$–$C_2$ alkyl), —$CH_2OH$, —$CH_2OCH_3$, —O($C_1$–$C_4$ alkyl), ($C_1$–$C_4$ alkyl)sulfanyl, ($C_1$–$C_4$ alkyl)sulfonyl, or ($C_1$–$C_4$ alkyl)sulfinyl, wherein said $C_1$–$C_6$ alkyl and $C_1$–$C_4$ alkyl moieties of the foregoing $R_3$ groups optionally contain one double or triple bond and are optionally substituted by from one to three substituents independently selected from hydroxy, amino, $C_1$–$C_3$ alkoxy, —NH($C_1$–$C_2$ alkyl), —N($C_1$–$C_2$ alkyl)$_2$, —$NHCOCH_3$, fluoro, chloro, and $C_1$–$C_3$ thioalkyl;

$R_4$ is hydrogen, $C_1$–$C_6$ alkyl, fluoro, chloro, bromo, iodo, $C_1$–$C_6$ alkoxy, formyl, trifluoromethoxy, —$CH_2OCH_3$, —$CH_2OCH_2CH_3$, —$CH_2CH_2OCH_3$, —$CH_2CF_3$, $CF_3$, amino, nitro, —NH($C_1$–$C_4$ alkyl), —N($CH_3$)$_2$, —$NHCOCH_3$, —$NHCONHCH_3$, ($C_1$–$C_4$ alkyl)sulfanyl, ($C_1$–$C_4$ alkyl)sulfinyl, ($C_1$–$C_4$ alkyl)sulfonyl, cyano, hydroxy, —CO($C_1$–$C_4$ alkyl), —CHO, or —$CO_2$($C_1$–$C_4$ alkyl), wherein said $C_1$–$C_6$ alkyl, $C_1$–$C_6$ alkoxy, and $C_1$–$C_4$ alkyl moieties of the foregoing $R_4$ groups optionally contain one double or triple bond and are optionally substituted with one substituent selected from hydroxy, amino, —$NHCOCH_3$, —NH($C_1$–$C_2$ alkyl), —N($C_1$–$C_2$ alkyl)$_2$, —$CO_2$($C_1$–$C_4$ alkyl), —CO ($C_1$–$C_4$ alkyl), $C_1$–$C_3$ alkoxy, ($C_1$–$C_3$ alkyl)sulfanyl, fluoro, chloro, cyano, and nitro;

$R_5$ is phenyl, naphthyl, thienyl, benzothienyl, pyridyl, quinolyl, pyrazinolyl, pyrimidyl, imidazolyl, furanyl, benzofuranyl, benzothiazolyl, isothiazolyl, benzoisothiazolyl, thiazolyl, isoxazolyl, benzisoxazolyl, benzimidazolyl, triazolyl, pyrazolyl, pyrrolyl, indolyl, azaindolyl, benzoxazolyl, oxazolyl, pyrrolidinyl, thiazolidinyl, morpholinyl, pyridinyl, tetrazolyl, or a 3- to 8-membered cycloalkyl ring or a 9- to 12-membered bicycloalkyl ring system, wherein said cycloalkyl ring and said bicycloalkyl ring system optionally contain one or two of O, S, or —N—G wherein G is hydrogen, $C_1$–$C_4$ alkyl, $C_1$–$C_4$ alkanoyl, phenyl, or benzyl, wherein each of the above $R_5$ groups is optionally substituted by up to three substituents independently selected from fluoro, chloro, $C_1$–$C_6$ alkyl, $C_1$–$C_6$ alkoxy, and trifluoromethyl, or one substituent selected from bromo, iodo, cyano, nitro, amino, —NH($C_1$–$C_4$ alkyl), —N($C_1$–$C_4$ alkyl)($C_1$–$C_2$ alkyl), —$CO_2$($C_1$–$C_4$ alkyl), —CO($C_1$–$C_4$ alkyl), —$SO_2NH$ ($C_1$–$C_4$ alkyl), —$SO_2N$($C_1$–$C_4$ alkyl)($C_1$–$C_2$ alkyl), —$SO_2NH_2$, —$NHSO_2$($C_1$–$C_4$ alkyl), —S($C_1$–$C_4$ alkyl), and —$SO_2$($C_1$–$C_4$ alkyl), wherein said $C_1$–$C_4$ alkyl and $C_1$–$C_6$ alkyl moieties of the foregoing $R_5$ groups optionally contain one double or triple bond and are optionally substituted by one or two substituents independently selected from fluoro, chloro, hydroxy, amino, methylamino, dimethylamino, and acetyl;

$R_6$ is hydrogen or $C_1$–$C_6$ alkyl, wherein said $C_1$–$C_6$ alkyl is optionally substituted by a single hydroxy, methoxy, ethoxy, or fluoro group;

$R_7$ is hydrogen, $C_1$–$C_4$ alkyl, fluoro, chloro, bromo, iodo, cyano, hydroxy, $C_1$–$C_4$ alkoxy, —CO($C_1$–$C_4$ alkyl), —$CO_2$($C_1$–$C_4$ alkyl), —$OCF_3$, $CF_3$, —$CH_2OH$, —$CH_2OCH_3$, or —$CH_2OCH_2CH_3$;

$R_8$ and $R_9$ are each, independently, hydrogen, hydroxy, methyl, ethyl, methoxy, or ethoxy;

or $R_8$ and $R^9$ together form an oxo (=O) group;

$R_{10}$ is hydrogen, $C_1$–$C_6$ alkyl, fluoro, chloro, bromo, iodo, $C_1$–$C_6$ alkoxy, formyl, amino, —NH($C_1$–$C_4$ alkyl), —N($C_1$–$C_4$ alkyl)($C_1$–$C_2$ alkyl), cyano, carboxy, amido, or —$SO_n$($C_1$–$C_4$ alkyl) wherein n is 0, 1, or 2, wherein said $C_1$–$C_6$ alkyl and $C_1$–$C_4$ alkyl moieties of the foregoing $R_{10}$ groups are optionally substituted by one of hydroxy, trifluoromethyl, amino, carboxy, amido, —NHCO($C_1$–$C_4$ alkyl), —NH($C_1$–$C_4$ alkyl), —N($C_1$–$C_4$ alkyl)($C_1$–$C_2$ alkyl), —$CO_2$($C_1$–$C_4$ alkyl), $C_1$–$C_3$ alkoxy, $C_1$–$C_3$ thioalkyl, fluoro, bromo, chloro, iodo, cyano, or nitro; and $R_{11}$ is hydrogen, hydroxy, fluoro, or methoxy.

DETAILED DESCRIPTION OF THE INVENTION

Improvement in QT dispersion by CRF antagonists by normalizing the parasympathetic and sympathetic electrical influence on the heart will result in decreased incidence of fatal ventricular arrhythmias resulting in reduced mortality. Similarly, CRF antagonists will reduce mortality by the improvement of heart rate variability through the same mechanism. Heart rate variability is the amount of fluctuations around the mean heart rate, and can be used as a correlate of the cardiorespiratory control system. Low heart rate variability, i.e., predominance of either the parasympathetic or sympathetic system, is associated with sudden cardiac death in diabetic, heart failure, and post-infarction patients and in many neurological disorders such as brain damage, Guillain-Barre syndrome, sudden infant death syndrome, congenital hypoventilation syndrome, uremic neuropathy, and the like. (see, e.g., Malpas et al., *Diabetes*, 39:1177–1181 (1990); Woo et al., *J. Am. Coll. Cardiol.*, 23:565–569 (1994); Bigger et al., *Circulation*, 85:164–171 (1992); and van Ravenswaaij-Arts et al., *Annals of Internal Medicine*, 118:436–447 (1993)).

CRF antagonists decrease the incidence of sudden death due to a centrally mediated imbalance in the neural outflow to the heart and respiratory system in a number of disorders. Patients at risk can be easily and inexpensively monitored by means of electrocardiogram QT dispersion and heart rate variability to determine if they would benefit from such therapy.

In addition to disease states, certain drugs administered to a patient to alleviate other symptoms may cause or result in QT dispersion and/or heart rate variability. Examples of such drugs include phenothiazine and atypical antipsychotics (e.g., chlorpromazine, respiradone), class 1A and class III antiarrhythmics (e.g., quinidine and sotolol), anesthetic agents (e.g., enflurane, isoflurane), and the like. In such a case, it may also be beneficial to administer a CRF antagonist in order to normalize the parasympathetic and sympathetic electrical influence on the heart and improve the QT dispersion and heart rate variability of the patient.

While the use of CRF antagonists alone will decrease the incidence of sudden death in certain patients, it may be preferable to combine the CRF antagonist with another drug. For example, other drugs that are also able to balance the neural outflow to heart and/or respiratory system may improve the efficacy of the CRF antagonist in a synergistic manner.

Preferred for use in the methods of the present invention are the compounds of formulas I and II, and their pharmaceutically acceptable salts, which are readily prepared. The compounds of formula II wherein A, D, and Y are N, a double bond connects E and D, and E is —$CR_4$, are prepared by one or more of the synthetic methods described in PCT publication WO 94/13677, referred to above. The compounds of formula II wherein A and Y are N, a double bond connects E and D, E is —$CR_4$, and D is —$CR_{10}$, are prepared by one or more of the synthetic methods described in PCT publication WO 94/13676, referred to above. The compounds of formula II wherein A is —$CR_7$, a double bond connects E and D, E is —$CR_4$, D is N or —$CR_{10}$, and Y is N, are prepared by one or more of the synthetic methods described in PCT publication WO 95/34563, referred to above. The remaining compounds of formula II and the compounds of formula I are prepared by one or more of the synthetic methods described in PCT publication WO 95/33750, referred to above. Additional information useful in preparing certain of the described compounds is provided in PCT/IB95/00437 (published as WO 96/39388), which described the production of certain intermediates.

Pharmaceutically acceptable salts of the compounds of formulas I and II include salts of acidic or basic groups. For example, pharmaceutically acceptable salts include sodium, calcium, and potassium salts of acidic groups, such as when the $R_{10}$ substituent is carboxy. Such salts are generally prepared by combining a compound of formula I or II with one molar equivalent of NaOH or KOH in a suitable solvent. Pharmaceutically acceptable acid addition salts of basic groups, such as amino groups, are formed by reacting the base form of a compound of formula I or II with an appropriate acid. Pharmaceutically acceptable salts of basic groups include hydrochloride, hydrobromide, sulfate, hydrogen sulfate, phosphate, hydrogen phosphate, dihydrogen phosphate, acetate, succinate, citrate, tartrate, lactate, mandelate, methanesulfonate (mesylate), and p-toluenesulfonate (tosylate) salts. When the salt is of a monobasic acid (e.g., the hydrochloride, the hydrobromide, the p-toluenesulfonate, the acetate), at least one molar equivalent and usually a molar excess of the acid is employed. However, when such salts as the sulfate, the hemisuccinate, the hydrogen phosphate, or the phosphate are desired, the appropriate and exact chemical equivalents of acid will generally be used. The free base and the acid are usually combined in a co-solvent from which the desired salt precipitates, or can be otherwise isolated by concentration or addition of a non-solvent.

Whenever reference is made herein to 3- to 8-membered cycloalkyl rings or 9- to 12-membered bicycloalkyl ring systems, each of which may optionally contain one or two of O, S, or —N—G, it is understood that the oxygen and sulfur atoms are not adjacent to each other in the cycloalkyl ring or bicycloalkyl ring system. When the cycloalkyl ring is three membered, it may only contain one of O, S, or —N—G. An example of a six-membered cycloalkyl ring having O and NH is morpholinyl.

Whenever $R_2$ or $R_5$ is a heterocyclic group, the group is attached through a carbon atom.

Formulas I and II, referred to above, are intended to include all stereoisomers (e.g., all geometric and optical isomers) as well as racemates of all compounds within the depicted genus.

In the methods of the invention, the compounds of formulas I and II, and their pharmaceutically acceptable salts, can be administered alone or in combination with pharmaceutically acceptable carriers, in either single or multiple doses. Suitable pharmaceutical carriers include inert solid diluents or fillers, sterile aqueous solutions, and various organic solvents. The pharmaceutical compositions formed by combining the active compounds and the pharmaceutically acceptable carriers are then readily administered in a variety of dosage forms such as tablets, powders, lozenges, syrups, injectable solutions, and the like. These pharmaceutical compositions can, if desired, contain additional ingredients such as flavorings, binders, excipients, and the like. Thus, for purposes of oral administration, tablets containing various excipients such as sodium citrate, calcium carbonate, and calcium phosphate may be employed along with various disintegrants such as starch, alginic acid, and certain complex silicates, together with binding agents such as polyvinylpyrrolidone, sucrose, gelatin, and acacia. Additionally, lubricating agents such as magnesium stearate, sodium lauryl sulfate, and talc are often useful for tabletting purposes. Solid compositions of a similar type can also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin, and combinations thereof. Oral administration is generally preferred. However, if the patient is unable to swallow, or oral absorption is otherwise impaired, another route of administration such as suppositories, parenteral, or topical administration will be appropriate.

For parenteral administration, solutions of the active compound in sesame or peanut oil, aqueous propylene glycol, or in sterile aqueous solution can be employed. Such aqueous solutions should be suitably buffered if necessary and the liquid diluent first rendered isotonic with sufficient saline or glucose. These particular aqueous solutions are especially suitable for intravenous, intramuscular, subcutaneous, and intraperitoneal administration. The sterile aqueous media employed are all readily available by standard techniques known to those skilled in the art.

For purposes of transdermal (e.g., topical) administration, dilute, sterile, aqueous or partially aqueous solutions (usually in about 0.1% to 5% concentration), otherwise similar to the above parenteral solutions, are employed.

Methods of preparing various pharmaceutical compositions with a certain amount of active ingredient are known, or will be apparent in light of this disclosure, to those skilled in the art. For example, see *Remington's Pharmaceutical Sciences,* Mack Publishing Company, Easton, Pa., 15th Edition (1975).

In the methods of the invention, the effective dosage for the compounds of formulas I and II, and their pharmaceutically acceptable salts, depends on the intended route of administration and other factors such as age and weight of the patient, as generally known to a physician. In general, the daily dosage will preferably be about 0.1 mg/kg to about 50 mg/kg of the body weight of the patient to be treated. More preferably, the daily dosage will be about 1.0 mg/kg to about 20 mg/kg of body weight. The daily dosage may be given in a single dose or in divided doses.

The methods of screening the compounds of formulas I and II, and their pharmaceutically acceptable salts, for CRF antagonist activity are as described in Wynn et al., *Endocrinology,* 116:1653–1659 (1985) and Grigoriadis et al., *Peptides,* 10:179–188 (1989). These methods determine the binding affinity of a test compound for a CRF receptor, which is highly related to its expected activity as a CRF antagonist. The binding affinities for the active compounds, expressed as $IC_{50}$ values, generally range from about 0.2 nanomolar to about 10 micromolar.

What is claimed is:

1. A method of reducing the incidence of sudden death in an animal comprising administering to said animal a therapeutically effective amount of a corticotropin releasing factor antagonist, wherein the risk of sudden death is related to the presence of a disease state in said animal, wherein said disease state is diabetes, neurological disorders, brain damage, Guillain-Barre syndrome, sudden infant death syndrome, congenital hypoventilation syndrome, or uremic neuropathy; and further wherein said corticotropin releasing factor antagonist is a compound of Formula I or II:

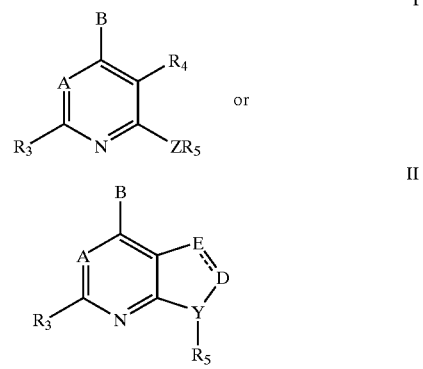

or a pharmaceutically acceptable salt thereof, wherein
the dashed line represents an optional double bond;
A is —$CR_7$ or N;
B is —$NR_1R_2$, —$CR_1R_2R_{11}$, —$C(=CR_1R_{12})R_2$, —$NHCR_{11}R_1R_2$, —$OCR_{11}R_1R_2$, —$SCR_{11}R_1R_2$, —$CR_{11}R_2OR_1$, —$CR_{11}R_2SR_1$, —$C(S)R_2$, —$NHNR_1R_2$, —$CR_2R_{11}NHR_1$ or —$C(O)R_2$;
D is
  N or —$CR_{10}$ when a double bond connects E and D and E is —$CR_4$;
  —$CR_{10}$ when a double bond connects E and D and E is N; or
  —$CR_8R_9$, —$CHR_{10}$, —$C=O$, —$C=S$, —$C=NH$, or —$C=NCH_3$ when a single bond connects E and D;
E is —$CR_4$ or N when a double bond connects E and D, and E is —$CR_4R_6$ or —$NR_6$ when a single bond connects E and D;
Y is N or —CH;
Z is NH, O, S, —$N(C_1-C_2$ alkyl), or —$CR_{12}R_{13}$, wherein $R_{12}$ and $R_{13}$ are each, independently, hydrogen, trifluoromethyl, or methyl, or one of $R_{12}$ and $R_{13}$ is cyano and the other is hydrogen or methyl;
$R_1$ is hydrogen or $C_1-C_6$ alkyl which is optionally substituted with up to two substituents independently selected from hydroxy, cyano, nitro, fluoro, chloro, bromo, iodo, $CF_3$, $C_1-C_4$ alkoxy, —O—CO—($C_1-C_4$ alkyl), —O—CO—NH($C_1-C_4$ alkyl), —O—CO—N ($C_1-C_4$ alkyl)($C_1-C_2$ alkyl), —NH($C_1-C_4$ alkyl), —N($C_1-C_2$ alkyl)($C_1-C_4$ alkyl), —S($C_1-C_4$ alkyl), —N($C_1-C_4$ alkyl)CO($C_1-C_4$ alkyl), —NHCO($C_1-C_4$ alkyl), —$CO_2$($C_1-C_4$ alkyl), —CONH($C_1-C_4$ alkyl), —CON($C_1-C_4$ alkyl)($C_1-C_2$ alkyl), ($C_1-C_4$ alkyl) sulfinyl, ($C_1-C_4$ alkyl)sulfonyl, and ($C_1-C_4$ alkyl) sulfanyl, and wherein said $C_1-C_6$ alkyl, $C_1-C_4$ alkoxy, and $C_1-C_4$ alkyl moieties in the foregoing $R_1$ groups optionally contain one double or triple bond;
$R_2$ is $C_1-C_6$ alkyl, heteroaryl, aryl, heteroaryl ($C_1-C_4$ alkyl), or aryl ($C_1-C_4$ alkyl), wherein said aryl and the aryl moiety of said (aryl)$C_1-C_4$ alkyl are selected from the group consisting of phenyl and naphthyl, and said heteroaryl and the heteroaryl moiety of said (heteroaryl)$C_1-C_4$ alkyl is selected from the group consisting of thienyl, benzothienyl, pyridyl, thiazolyl, quinolyl, pyrazinyl, pyrimidyl, imidazolyl, furanyl, benzofuranyl, benzothiazolyl, isothiazolyl, benzisothiazolyl, benzisoxazolyl, benzimidazolyl, indolyl, and benzoxazolyl; or $R^2$ is $C_3$–$C_8$ cycloalkyl or ($C_3$–$C_8$ cycloalkyl)$C_1$–$C_6$ alkyl, wherein one or two of the ring carbons of said cycloalkyl having at least 4 ring members and the cycloalkyl moiety of said ($C_3$–$C_8$ cycloalkyl)$C_1$–$C_6$ alkyl having at least 4 ring members is optionally replaced by an oxygen or sulfur atom or by —$NR_4$ wherein $R_{14}$ is hydrogen or $C_1$–$C_4$ alkyl; and wherein each of the foregoing $R_2$ groups is optionally substituted by up to three substituents independently selected from chloro, fluoro, and $C_1$–$C_4$ alkyl, or by one substituent selected from bromo, iodo, cyano, nitro, $C_1$–$C_6$ alkoxy, —O—CO—($C_1$–$C_4$ alkyl), —O—CO—N($C_1$–$C_4$ alkyl)($C_1$–$C_2$ alkyl), —$CO_2$ ($C_1$–$C_4$ alkyl), ($C_1$–$C_4$ alkyl)sulfanyl, ($C_1$–$C_4$ alkyl)sulfinyl, and ($C_1$–$C_4$ alkyl)sulfonyl, and wherein said $C_1$–$C_4$ alkyl and $C_1$–$C_6$ alkyl moieties of the foregoing $R_2$ groups optionally contain one carbon-carbon double or triple bond;

or $R^1$ and $R^2$ of said —$NR_1R_2$ and said —$CR_1R_2R_{11}$ are taken together to form a saturated or partially saturated 5- to 8-membered ring, wherein said ring optionally contains one or two carbon-carbon double bonds, and wherein one or two of the ring carbons is optionally replaced by a heteroatom selected from O, S, and N;

$R_3$ is hydrogen, $C_1$–$C_6$ alkyl, fluoro, chloro, bromo, iodo, hydroxy, amino, SH, —NH($C_1$–$C_4$ alkyl), —N($C_1$–$C_4$ alkyl)($C_1$–$C_2$ alkyl), —$CH_2OH$, —$CH_2OCH_3$, —O($C_1$–$C_4$ alkyl), ($C_1$–$C_4$ alkyl)sulfanyl, ($C_1$–$C_4$ alkyl)sulfonyl, or ($C_1$–$C_4$ alkyl)sulfinyl, wherein said $C_1$–$C_6$ alkyl and $C_1$–$C_4$ alkyl moieties of the foregoing $R_3$ groups optionally contain one double or triple bond and are optionally substituted by from one to three substituents independently selected from hydroxy, amino, $C_1$–$C_3$ alkoxy, —NH($C_1$–$C_2$ alkyl), —N($C_1$–$C_2$ alkyl)$_2$, —$NHCOCH_3$, fluoro, chloro, and $C_1$–$C_3$ thioalkyl;

$R_4$ is hydrogen, $C_1$–$C_6$ alkyl, fluoro, chloro, bromo, iodo, $C_1$–$C_6$ alkoxy, formyl, trifluoromethoxy, —$CH_2OCH_3$, —$CH_2OCH_2CH_3$, —$CH_2CH_2OCH_3$, —$CH_2CF_3$, $CF_3$, amino, nitro, —NH($C_1$–$C_4$ alkyl), —N($CH_3$)$_2$, —$NHCOCH_3$, —$NHCONHCH_3$, ($C_1$–$C_4$ alkyl)sulfanyl, ($C_1$–$C_4$ alkyl)sulfinyl, ($C_1$–$C_4$ alkyl)sulfonyl, cyano, hydroxy, —CO($C_1$–$C_4$ alkyl), —CHO, or —$CO_2$($C_1$–$C_4$ alkyl), wherein said $C_1$–$C_6$ alkyl, $C_1$–$C_6$ alkoxy, and $C_1$–$C_4$ alkyl moieties of the foregoing $R_4$ groups optionally contain one double or triple bond and are optionally substituted with one substituent selected from hydroxy, amino, —$NHCOCH_3$, —NH($C_1$–$C_2$ alkyl), —N($C_1$–$C_2$ alkyl)$_2$, —$CO_2$($C_1$–$C_4$ alkyl), —CO ($C_1$–$C_4$ alkyl), $C_1$–$C_3$ alkoxy, ($C_1$–$C_3$ alkyl)sulfanyl, fluoro, chloro, cyano, and nitro;

$R_5$ is phenyl, naphthyl, thienyl, benzothienyl, pyridyl, quinolyl, pyrazinolyl, pyrimidyl, imidazolyl, furanyl, benzofuranyl, benzothiazolyl, isothiazolyl, benzoisothiazolyl, thiazolyl, isoxazolyl, benzisoxazolyl, benzimidazolyl, triazolyl, pyrazolyl, pyrrolyl, indolyl, azaindolyl, benzoxazolyl, oxazolyl, pyrrolidinyl, thiazolidinyl, morpholinyl, pyridinyl, tetrazolyl, or a 3- to 8-membered cycloalkyl ring or a 9- to 12-membered bicycloalkyl ring system, wherein said cycloalkyl ring and said bicycloalkyl ring system optionally contain one or two of O, S, or —N—G wherein G is hydrogen, $C_1$–$C_4$ alkyl, $C_1$–$C_4$ alkanoyl, phenyl, or benzyl, wherein each of the above $R_5$ groups is optionally substituted by up to three substituents independently selected from fluoro, chloro, $C_1$–$C_6$ alkyl, $C_1$–$C_6$ alkoxy, and trifluoromethyl, or one substituent selected from bromo, iodo, cyano, nitro, amino, —NH($C_1$–$C_4$ alkyl), —N($C_1$–$C_4$ alkyl)($C_1$–$C_2$ alkyl), —$CO_2$($C_1$–$C_4$ alkyl), —CO($C_1$–$C_4$ alkyl), —$SO_2NH$ ($C_1$–$C_4$ alkyl), —$SO_2N$($C_1$–$C_4$ alkyl)($C_1$–$C_2$ alkyl), —$SO_2NH_2$, —$NHSO_2$($C_1$–$C_4$ alkyl), —S($C_1$–$C_4$ alkyl), and —$SO_2$($C_1$–$C_4$ alkyl), wherein said $C_1$–$C_4$ alkyl and $C_1$–$C_6$ alkyl moieties of the foregoing $R_5$ groups optionally contain one double or triple bond and are optionally substituted by one or two substituents independently selected from fluoro, chloro, hydroxy, amino, methylamino, dimethylamino, and acetyl;

$R_6$ is hydrogen or $C_1$–$C_6$ alkyl, wherein said $C_1$–$C_6$ alkyl is optionally substituted by a single hydroxy, methoxy, ethoxy, or fluoro group;

$R_7$ is hydrogen, $C_1$–$C_4$ alkyl, fluoro, chloro, bromo, iodo, cyano, hydroxy, $C_1$–$C_4$ alkoxy, —CO($C_1$–$C_4$ alkyl), —$CO_2$($C_1$–$C_4$ alkyl), —$OCF_3$, $CF_3$, —$CH_2OH$, —$CH_2OCH_3$, or —$CH_2OCH_2CH_3$;

$R_8$ and $R_9$ are each, independently, hydrogen, hydroxy, methyl, ethyl, methoxy, or ethoxy;

or $R_8$ and $R_9$ together form an oxo (=O) group;

$R_{10}$ is hydrogen, $C_1$–$C_6$ alkyl, fluoro, chloro, bromo, iodo, $C_1$–$C_6$ alkoxy, formyl, amino, —NH($C_1$–$C_4$ alkyl), —N($C_1$–$C_4$ alkyl)($C_1$–$C_2$ alkyl), cyano, carboxy, amido, or —$SO_n$($C_1$–$C_4$ alkyl) wherein n is 0, 1, or 2, wherein said $C_1$–$C_6$ alkyl and $C_1$–$C_4$ alkyl moieties of the foregoing $R_{10}$ groups are optionally substituted by one of hydroxy, trifluoromethyl, amino, carboxy, amido, —NHCO($C_1$–$C_4$ alkyl), —NH($C_1$–$C_4$ alkyl), —N($C_1$–$C_4$ alkyl)($C_1$–$C_2$ alkyl), —$CO_2$($C_1$–$C_4$ alkyl), $C_1$–$C_3$ alkoxy, $C_1$–$C_3$ thioalkyl, fluoro, bromo, chloro, iodo, cyano, or nitro; and $R_{11}$ is hydrogen, hydroxy, fluoro, or methoxy.

2. The method of claim 1 wherein B is —$NR_1R_2$, —$NHCHR_1R_2$, —$CR_1R_2R_{11}$, —$SCHR_1R_2$, or —$OCHR_1R_2$; $R_1$ is $C_1$–$C_6$ alkyl optionally substituted with a single hydroxy, fluoro, or $C_1$–$C_2$ alkoxy group and optionally containing one carbon-carbon double or triple bond; $R_2$ is benzyl or $C_1$–$C_6$ alkyl optionally containing one carbon-carbon double or triple bond, wherein said $C_1$–$C_6$ alkyl and the phenyl moiety of said benzyl are optionally substituted with fluoro, $C_1$–$C_2$ alkyl, or $C_1$–$C_2$ alkoxy; and $R_{11}$ is hydrogen or fluoro.

3. The method of claim 1 wherein $R_2$ is (aryl)$C_1$–$C_4$ alkyl or (heteroaryl)$C_1$–$C_4$ alkyl in which said aryl moiety is phenyl, furanyl, or benzofuranyl, and said heteroaryl moiety is thienyl, benzothienyl, thiazolyl, pyridyl, or benzothiazolyl.

4. The method of claim 1 wherein B is $NR_1R_2$ or $CHR_1R_2$ in which $R_1$ and $R_2$ are taken together with N or CH to form a 5- or 6-membered ring optionally having sulfur, oxygen, or, where B is $NR_1R_2$, one more nitrogen in said ring.

5. The method of claim 1 wherein B is —$NHCHR_1R_2$ or —$OCHR_1R_2$, wherein the $CHR_1R_2$ moiety is a 5- or 6-membered ring optionally containing one oxygen or sulfur.

6. The method of claim 5 wherein B is tetrahydrofuranyl, tetrahydrothiafuranyl, tetrahydrothienyl, thiazolidinyl, or cyclopentanyl.

7. The method of claim 1 wherein $R_3$ is methyl, chloro, or methoxy; $R_4$ is methyl, —$CH_2OH$, cyano, trifluoromethoxy, methoxy, trifluoromethyl, chloro, —$CO_2CH_3$, —$CH_2OCH_3$, —$CH_2Cl$, —$CH_2F$, amino, or nitro; $R_6$ is hydrogen, methylsulfinyl, methylsulfanyl, methylsulfonyl, or ethyl; and $R_5$ is phenyl or pyridyl wherein said phenyl or pyridyl is substituted by one substituent independently selected from fluoro, chloro, bromo, iodo, $C_1$–$C_4$ alkoxy, trifluoromethyl, $C_1$–$C_3$ hydroxyalkyl, —$CO_2$($C_1$–$C_2$ alkyl), $C_1$–$C_2$ alkylamino, —CO($C_1$–$C_4$ alkyl), and $C_1$–$C_6$ alkyl, wherein said $C_1$–$C_6$ alkyl and said $C_1$–$C_4$ alkyl are optionally substituted by a single hydroxy or fluoro group and optionally contain one carbon-carbon double or triple bond.

8. The method of claim 1 wherein the compound of formula I or II is selected from the group consisting of:

4-(1-ethyl-propoxy)-2,5-dimethyl-6-(2,4,6-trimethyl-benzyl)-pyrimidine;
2-(4-bromo-2,6-dimethyl-phenoxy)-4-(1-ethyl-propoxy)-3,6-dimethyl-pyridine;
2-(4-ethyl-2,6-dimethyl-phenoxy)-4-(1-ethyl-propoxy)-3,6-dimethyl-pyridine;
3-ethyl-4-(1-ethyl-propoxy)-6-methyl-2-(2,4,6-trimethyl-phenoxy)-pyridine;
2-(2,6-dimethyl-4-propyl-phenoxy)-4-(1-ethyl-propoxy)-3,6-dimethyl-pyridine;
4-(1-ethyl-propoxy)-2-(4-methoxy-2,6-dimethyl-phenoxy)-3,6-dimethyl-pyridine;
2-(4-ethoxy-2,6-dimethyl-phenoxy)-4-(1-ethyl-propoxy)-3,6-dimethyl-pyridine;
2-(4-chloro-2,6-dimethyl-phenoxy)-4-(1-ethyl-propoxy)-3,6-dimethyl-pyridine;
4-(1-methoxymethyl-propoxy)-3,6-dimethyl-2-(2,4,6-trimethyl-phenoxy)-pyridine;
[3,6-dimethyl-2-(2,4,6-trimethyl-phenoxy)-pyridin-4-yl]-diethyl-amine;
[3,6-dimethyl-2-(2,4,6-timethyl-phenoxy)-pyridin-4-yl]-ethyl-propyl-amine;
[2,5-dimethyl-6-(2,4,6-trimethyl-phenoxy)-pyrimidin-4-yl](1-ethyl-propyl)-amine;
butyl-[3,6-dimethyl-2-(2,4,6-trimethyl-phenoxy)-pyridin-4-yl]-ethyl-amine;
4-(1-ethyl-propoxy)-3,6-dimethyl-2-(2,4,6-trimethyl-phenylsulfanyl)-pyridine;
butyl-[2-(4-chloro-2,6-dimethyl-phenoxy)-3,6-dimethyl-pyridin-4-yl]-ethyl-amine;
4-(1-ethyl-propylamino)-6-methyl-2-(2,4,6-trimethyl-phenoxy)-nicotinic acid methyl ester;
[3,6-dimethyl-2-(2,4,6-trimethyl-phenylsulfanyl)-pyridin-4-yl]-ethyl-propyl-amine;
[4-(1-ethyl-propylamino)-6-methyl-2-(2,4,6-trimethyl-phenoxy)-pyridin-3-yl]-methanol;
[2-(4-chloro-2,6-dimethyl-phenoxy)-3,6-dimethyl-pyridin-4-yl]-ethyl-propyl-amine;
1-(ethyl-propyl)-[6-methyl-3-nitro-2-(2,4,6-trimethylphenoxy)-pyridin-4-yl]-amine;
N4-(1-ethyl-propyl)-6-methyl-3-nitro-N2-(2,4,6-trimethyl-phenyl)-pyridine-2,4-diamine;
N4-(1-ethyl-propyl)-6-methyl-2-(2,4,6-trimethyl-phenoxy)-pyridine-3,4-diamine;
N4-(1-ethyl-propyl)-6-methyl-N2-(2,4,6-trimethyl-phenyl)-pyridine-2,3,4-triamine;
[3,6-dimethyl-2-(2,4,6-trimethyl-phenoxy)-pyridin-4-yl]-ethyl-(2,2,2-trifluoro-ethyl)-amine;
[3-chloromethyl-6-methyl-2-(2,4,6-trimethyl-phenoxy)pyridin-4-yl]-(1-ethyl-propyl)-amine;
[3,6-dimethyl-2-(2,4,6-trimethyl-phenoxy)-pyridin-4-yl]-(1-ethyl-propyl)-amine;
(1-ethyl-propyl)-[2-methyl-5-nitro-6-(2,4,6-trimethyl-pyridin-3-yloxy)-pyrimidin-4-yl]-amine;
(1-ethyl-propyl)-[3-methoxymethyl-6-methyl-2-(2,4,6-trimethyl-phenoxy)-pyridin-4-yl]-amine;
N-(1-ethyl-propyl)-2-methyl-5-nitro-N-(2,4,6-trimethyl-pyridin-3-yl)-pyrimidine-4,6-diamine;
[2-(4-chloro-2,6-dimethyl-phenoxy)-3,6-dimethyl-pyridin-4-yl]-diethyl-amine;
4-(1-ethyl-propoxy)-3,6-dimethyl-2-(2,4,6-trimethylphenoxy)-pyridine;
butyl-[2,5-dimethyl-7-(2,4,6-trimethylphenyl)-6,7-dihydro-5H-pyrrolo[2,3-d]pyrimidin4-yl]-ethyl-amine;
4-(butyl-ethylamino)-2,5-dimethyl-7-(2,4,6-trimethylphenyl)-5,7-dihydro-pyrrolo[2,3-d]pyrimidin-6-one;
4-(1-ethylpropoxy)-2,5-dimethyl-6-(2,4,6-trimethylphenoxy)-pyrimidine;
N-butyl-N-ethyl-2,5-dimethyl-N-(2,4,6-trimethylphenyl)-pyrimidine-4,6-diamine;
(1-ethyl-propyl)-[5-methyl-3-(2,4,6-trimethyl-phenyl)-3H-imidazo[4,5-b]pyridin-7-yl]-amine;
[2,5-dimethyl-3-(2,4,6-trimethyl-phenyl)-3H-imidazo[4,5-b]pyridin-7-yl]-(1-ethyl-propyl)-amine;
N4-(1-ethyl-propyl)-6,N3-dimethyl-2-(2,4,6-trimethylphenoxy)-pyridine-3,4-diamine;
N4-(1-ethyl-propyl)-6,N3,N3-trimethyl-2-(2,4,6-trimethylphenoxy)-pyridine-3,4-diamine;
6-(1-ethyl-propoxy)-2-methyl-N4-(2,4,6-trimethyl-phenyl)-pyrimidine-4,5-diamine;
[4-(1-ethyl-propoxy)-3,6-dimethyl-pyridin-2-yl]-(2,4,6-trimethylphenyl)-amine; and
6-(ethyl-propyl-amino)-2,7-dimethyl-9-(2,4,6-trimethylphenyl)-7,9-dihydro-purin-8-one.

9. A method of claim 8 wherein said compound is [3,6-dimethyl-2-(2,4,6-trimethyl-phenoxy)-pyridin-4-yl]-(1-ethyl-propyl)-amine.

10. A method of claim 8 wherein said compound is 4-(1-ethyl-propoxy)-3,6-methyl-2-(2,4,6-trimethylphenoxy)-pyridine.

11. The method of claim 1 wherein said compound is a compound of formula II in which E and D are connected by a double bond, E is —$CR_4$, D is —$CR_{10}$ or N, Y is N, and A is —$CR_7$.

12. The method of claim 11 wherein said compound is selected from the group consisting of:

butyl-[3,6-dimethyl-1-(2,4,6-trimethylphenyl)-1H-pyrazolo[3,4-b]pyridin-4-yl]-ethylamine;
3,6-dimethyl4-(tetrahydrofuran-3-yloxy)-1-(2,4,6-trimethylphenyl)-1H-pyrazolo[3,4-b]pyridine;
[3,6-dimethyl-1-(2,4,6-trimethylphenyl)-1H-pyrazolo[3,4,b]pyridin-4-yl]-(1-methoxymethylpropyl)-amine;
4-(1-methoxymethylpropoxy)-3,6-dimethyl-1-(2,4,6-trimethylphenyl)-1H-pyrazolo[3,4-b]pyridine;
(1-ethylpropyl)-[3,5,6-trimethyl-1-(2,4,6-trimethylphenyl)-1H-pyrazolo[3,4-b]pyridin-4-yl]-amine;
4-(1-ethylpropoxy)-2,5-dimethyl-7-(2,4,6-trimethylphenyl)-7H-pyrrolo[2,3-b]pyridine;
4-(1-ethylpropoxy)-2,5,6-trimethyl-7-(2,4,6-trimethylphenyl)-7H-pyrrolo[2,3-b]pyridine; and
4-(1-ethylpropoxy)-2,5-dimethyl-7-(2,6-dimethyl-4-bromophenyl)-7H-pyrrolo[2,3-b]pyridine.

13. The method of claim 1 wherein said compound is a compound of formula II in which E and D are connected by a double bond, E is —$CR_4$, and D, Y, and A are N.

14. The method of claim 13 wherein said compound is selected from the group consisting of:

3-{(4-methyl-benzyl)-[3,6-dimethyl-1-(2,4,6-trimethylphenyl)-1H-pyrazolo[3,4-d]pyrimidin4-yl]-amino}-propan-1-ol;
diethyl-[6-methyl-3-methylsulfanyl-1-(2,4,6-trichlorophenyl)-1H-pyrazolo[3,4-d]pyrimidin-4-yl]-amine;

2-{butyl-[6-methyl-3-methylsulfanyl-1-(2,4,6-trichlorophenyl)-1H-pyrazolo[3,4-d]pyrimidin-4-yl]-amino}-ethanol;

dibutyl-[6-methyl-3-methylsulfanyl-1-(2,4,6-trichlorophenyl)-1H-pyrazolo[3,4-d]pyrimidin-4-yl}-amine;

butyl-ethyl-[6-methyl-3-methylsulfanyl-1-(2,4,6-trichlorophenyl)-1H-pyrazolo[3,4-d]pyrimidin-4-yl]-amine;

butyl-ethyl-[6-methyl-3-methylsulfonyl-1-(2,4,6-trichlorophenyl)-1H-pyrazolo[3,4-d]pyrimidin-4-yl]-amine;

butyl-cyclopropylmethyl-[6-methyl-3-methylsulfanyl-1-(2,4,6-trichlorophenyl)-1H-pyrazolo[3,4-d]pyrimidin-4-yl]-amine;

di-1-propyl-[6-methyl-3-methylsulfanyl-1-(2,4,6-trichlorophenyl)-1H-pyrazolo[3,4-d]pyrimidin-4-yl]-amine;

diallyl-[6-methyl-3-methylsulfanyl-1-(2,4,6-trichlorophenyl)-1H-pyrazolo[3,4-d]pyrimidin-4-yl]-amine;

butyl-ethyl-[6-chloro-3-methylsulfanyl-1-(2,4,6-trichlorophenyl)-1H-pyrazolo[3,4-d]pyrimidin-4-yl]-amine;

butyl-ethyl-[6-methoxy-3-methylsulfanyl-1-(2,4,6-trichlorophenyl)-1H-pyrazolo[3,4-d]pyrimidin-4-yl]-amine;

propyl-ethyl-[3,6-dimethyl-1-(2,4,6-trimethylphenyl)-1H-pyrazolo[3,4-d]pyrimidin-4-yl]-amine;

4-(1-ethyl-propyl)-6-methyl-3-methylsulfanyl-1-(2,4,6-trimethylphenyl)-1H-pyrazolo[3,4-d]pyrimidine;

2-[3,6-dimethyl-1-(2,4,6-trimethylphenyl)-1H-pyrazolo[3,4-d]pyrimidin-4-ylamine]-butan-1-ol;

[3,6-dimethyl-1-(2,4,6-trimethylphenyl)-1H-pyrazolo-[3,4-d]pyrimidin-4-yl]-(1-methylpropyl)amine; and 4-(1-methoxymethylpropoxy)-3,6-dimethyl-1-(2,4,6-trimethylphenyl)-1H-pyrazolo[3,4-d]pyrimidine.

15. The method of claim 1 wherein said compound is a compound of formula II in which E and D are connected by a double bond, E is —CR$_4$, D is —CR$_{10}$, and Y and A are N.

16. The method of claim 15 wherein said compound is selected from the group consisting of:

n-butyl-ethyl-[2,5-dimethyl-7-(2,4,6-trimethylphenyl)-7H-pyrrolo[2,3-d]pyrimidin-4-yl]amine;

di-n-propyl-[2,5-dimethyl-7-(2,4,6-trimethylphenyl)-7H-pyrrolo[2,3-d]pyrimidin-4-yl]amine;

ethyl-n-propyl-[2,5-dimethyl-7-(2,4,6-trimethylphenyl)-7H-pyrrolo[2,3-d]pyrimidin-4-yl]amine;

diethyl-2,5-dimethyl-7-(2,4,6-trimethylphenyl)-7H-pyrrolo[2,3-d]pyrimidin-4-yl]amine;

n-butyl-ethyl-[2,5,6-trimethyl-7-(2,4,6-trimethylphenyl)-7H-pyrrolo[2,3-d]pyrimidin-4-yl]amine;

2-{N-n-butyl-N-[2,5-dimethyl-7-(2,4,6-trimethylphenyl)-7H-pyrrolo[2,3-d]pyrimidin-4-yl]amino}-ethanol;

4-(1-ethyl-propyl)-2,5,6-trimethyl-7-(2,4,6-trimethylphenyl)-7H-pyrrolo[2,3-d]pyrimidine;

n-butyl-ethyl-[2,5-dimethyl-7-(2,4-dimethylphenyl)-7H-pyrrolo[2,3-d]pyrimidin-4-yl]amine;

2,5-dimethyl-7-(2,4,6-trimethylphenyl)-7H-pyrrolo[2,3-d]pyrimidyl-4-yl]-(1-ethyl-propyl)amine;

2-[7-(4-bromo-2,6-dimethylphenyl)-2,5-dimethyl-7H-pyrrolo[2,3-d]pyrimidin-4-ylamino]-butan-1-ol;

2-(S)-[7-(4-bromo-2,6-dimethylphenyl)-2,5-dimethyl-7H-pyrrolo[2,3-d]pyrimidin-4-ylamino]-butan-1-ol;

4-(1-ethyl-propoxy)-2,5,6-trimethyl-7-(2,4,6-trimethylphenyl)-7H-pyrrolo[2,3-d]pyrimidine;

4-(1-methoxymethyl-propoxy)-2,5,6-trimethyl-7-(2,4,6-trimethylphenyl)-7H-pyrrolo[2,3-d]pyrimidine;

4-(1-ethyl-butyl)-2,5,6-trimethyl-7-(2,4,6-trimethylphenyl)-7H-pyrrolo-[2,3-d]pyrimidine;

[7-(4-bromo-2,6-dimethyl-phenyl)-2,5-dimethyl-7H-pyrrolo[2,3-d]pyrimidin-4-yl]-(1-methoxymethyl-propyl)-amine;

2-[7-(2-bromo-4,6-dimethyl-phenyl)-2,5-dimethyl-7H-pyrrolo[2,3-d]pyrimidin-4-ylamino]-butan-1-ol;

2-[7-(4-ethyl-2,6-dimethyl-phenyl)-2,5-dimethyl-7H-pyrrolo[2,3-d]pyrimidin-4-ylamino]-butan-1-ol;

2-[7-(2-ethyl-4,6-dimethylphenyl)-2,5-dimethyl-7H-pyrrolo[2,3-d]pyrimidin-4-ylamino]-butan-1-ol; and 2-[7-(2-fluoromethyl-4,6-dimethylphenyl)-2,5-dimethyl-7H-pyrrolo[2,3-d]pyrimidin-4-ylamino]-butan-1-ol.

* * * * *